United States Patent
Adams et al.

(10) Patent No.: US 10,952,703 B2
(45) Date of Patent: Mar. 23, 2021

(54) BROADBAND BLENDED FUNDAMENTAL AND HARMONIC FREQUENCY ULTRASONIC DIAGNOSTIC IMAGING

(71) Applicant: KONINKLIJKE PHILIPS N.V., Eindhoven (NL)

(72) Inventors: Darwin Philip Adams, Eindhoven (NL); Scott William Dianis, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 359 days.

(21) Appl. No.: 15/546,017

(22) PCT Filed: Jan. 18, 2016

(86) PCT No.: PCT/IB2016/050216
§ 371 (c)(1),
(2) Date: Jul. 25, 2017

(87) PCT Pub. No.: WO2016/120745
PCT Pub. Date: Aug. 4, 2016

(65) Prior Publication Data
US 2018/0000452 A1    Jan. 4, 2018

Related U.S. Application Data

(60) Provisional application No. 62/109,121, filed on Jan. 29, 2015.

(51) Int. Cl.
*A61B 8/00* (2006.01)
*G01S 7/52* (2006.01)
*G01S 15/89* (2006.01)

(52) U.S. Cl.
CPC ........ *A61B 8/4488* (2013.01); *G01S 7/52025* (2013.01); *G01S 7/52038* (2013.01);
(Continued)

(58) Field of Classification Search
CPC ......... A61B 8/4488; A61B 8/54; A61B 8/481; G01S 7/52025; G01S 7/52038;
(Continued)

(56) References Cited

U.S. PATENT DOCUMENTS 4,561,019 A * 12/1985 Lizzi ........................ G01S 7/10
348/163
5,526,816 A *  6/1996 Arditi ..................... A61B 8/481
600/458
(Continued)

FOREIGN PATENT DOCUMENTS

CN      101642379 A     2/2010
JP      2003-230559   *  8/2003
(Continued)

OTHER PUBLICATIONS

English Translation of JP2003-230559.*

*Primary Examiner* — Helen C Kwok

(57) ABSTRACT

An ultrasound system is described which produces blended fundamental and harmonic frequency images. Successively transmitted, differently modulated pulses are transmitted by an ultrasound probe and both fundamental and harmonic frequencies are received in response. The echo signals received from the two pulses are processed by pulse inversion, producing cleanly separated bands of fundamental and harmonic signals in which undesired components have been cancelled. Since the two bands have been separated by signal cancellation rather than filtering, the two bands are allowed to overlap, providing broadband signals in each band. The bands are filtered by bandpass filtering to define the fundamental and harmonic signals to be imaged. The signals are detected, and the detected signals are combined after weighting to produce a blended fundamental/harmonic image.

15 Claims, 3 Drawing Sheets

(52) U.S. Cl.
CPC ...... *G01S 7/52095* (2013.01); *G01S 15/8954* (2013.01); *G01S 15/8963* (2013.01)

(58) Field of Classification Search
CPC ............ G01S 7/52095; G01S 7/52039; G01S 7/52077; G01S 7/52085; G01S 15/8954; G01S 15/8963; G01S 15/8959
See application file for complete search history.

(56) References Cited

U.S. PATENT DOCUMENTS

| | | | | |
|---|---|---|---|---|
| 5,579,768 | A * | 12/1996 | Klesenski | G01S 7/52033 600/442 |
| 5,628,322 | A * | 5/1997 | Mine | G01N 29/036 600/453 |
| 5,706,819 | A * | 1/1998 | Hwang | A61B 8/06 600/458 |
| 5,897,500 | A * | 4/1999 | Zhao | G01S 7/52074 600/443 |
| 5,961,460 | A * | 10/1999 | Guracar | A61B 8/14 600/440 |
| 6,023,977 | A * | 2/2000 | Langdon | G01N 29/06 367/87 |
| 6,048,316 | A * | 4/2000 | Zhao | G01S 7/52034 600/447 |
| 6,050,942 | A * | 4/2000 | Rust | G01S 7/52026 600/437 |
| 6,095,980 | A * | 8/2000 | Burns | A61B 8/481 600/453 |
| 6,132,374 | A * | 10/2000 | Hossack | A61B 8/00 600/443 |
| 6,146,330 | A * | 11/2000 | Tujino | G01S 7/52038 600/443 |
| 6,179,781 | B1 * | 1/2001 | Phillips | A61B 8/06 600/454 |
| 6,213,947 | B1 * | 4/2001 | Phillips | G01S 7/52038 600/443 |
| 6,231,512 | B1 * | 5/2001 | Chiao | G01S 7/52033 600/447 |
| 6,283,919 | B1 | 9/2001 | Roundhill et al. | |
| 6,312,379 | B1 * | 11/2001 | Bradley | G01S 7/52039 600/437 |
| 6,319,203 | B1 * | 11/2001 | Averkiou | G01S 7/52038 600/443 |
| 6,401,539 | B1 * | 6/2002 | Langdon | G01N 29/06 73/609 |
| 6,443,896 | B1 | 9/2002 | Detmer | |
| 6,454,714 | B1 * | 9/2002 | Ng | A61B 8/06 600/443 |
| 6,458,083 | B1 * | 10/2002 | Jago | A61B 8/08 600/443 |
| 6,516,667 | B1 * | 2/2003 | Broad | G01S 7/52025 600/443 |
| 6,530,885 | B1 | 3/2003 | Entrekin et al. | |
| 6,638,228 | B1 * | 10/2003 | Brock-Fisher | G01S 7/52025 600/443 |
| 7,044,914 | B2 * | 5/2006 | Kawagishi | G01S 7/52038 600/458 |
| 7,056,290 | B2 * | 6/2006 | Rielly | A61B 8/481 600/447 |
| 7,338,448 | B2 * | 3/2008 | Hao | G01S 7/52038 600/443 |
| 8,137,272 | B2 | 3/2012 | Cooley et al. | |
| 8,454,517 | B2 * | 6/2013 | Sato | G01S 7/52039 600/458 |
| 8,740,799 | B2 | 6/2014 | Itani | |
| 8,852,108 | B2 * | 10/2014 | Hashiba | G01S 7/52038 600/437 |
| 9,370,338 | B2 * | 6/2016 | Hashiba | A61B 8/08 |
| 9,398,880 | B2 † | 7/2016 | Barnett | |
| 2002/0040188 | A1 * | 4/2002 | Averkiou | G01S 7/52038 600/458 |
| 2002/0128555 | A1 * | 9/2002 | Maxwell | A61B 8/54 600/447 |
| 2003/0114758 | A1 * | 6/2003 | Jensen | G01S 7/52038 600/437 |
| 2003/0216644 | A1 * | 11/2003 | Hall | A61B 8/08 600/443 |
| 2004/0059218 | A1 * | 3/2004 | Kanda | A61B 8/06 600/443 |
| 2005/0054928 | A1 * | 3/2005 | Cerofolini | G01N 29/06 367/87 |
| 2005/0124895 | A1 * | 6/2005 | Jensen | G01S 7/52038 600/443 |
| 2008/0229833 | A1 * | 9/2008 | Asafusa | G01S 7/52047 73/627 |
| 2008/0234580 | A1 * | 9/2008 | Bruce | G01S 7/52038 600/458 |
| 2008/0275338 | A1 * | 11/2008 | Jensen | A61B 8/481 600/437 |
| 2010/0036255 | A1 | 2/2010 | Itani | |
| 2010/0298710 | A1 * | 11/2010 | Averkiou | A61B 8/481 600/458 |
| 2013/0144172 | A1 * | 6/2013 | Hashiba | A61B 8/08 600/458 |
| 2013/0208562 | A1 * | 8/2013 | Shen | G01S 15/8954 367/7 |
| 2014/0254307 | A1 * | 9/2014 | Zhao | G01S 7/523 367/7 |
| 2016/0166237 | A1 * | 6/2016 | Yoshiara | A61B 8/5207 600/443 |

FOREIGN PATENT DOCUMENTS

| | | |
|---|---|---|
| JP | 2007167626 A | 7/2007 |
| JP | 2009090134 A | 4/2009 |

\* cited by examiner
† cited by third party

BROADBAND BLENDED FUNDAMENTAL AND HARMONIC FREQUENCY ULTRASONIC DIAGNOSTIC IMAGING

This application is the U.S. National Phase application under 35 U.S.C. § 371 of International Application No. PCT/IB2016/050216, filed on Jan. 18, 2016, which claims the benefit of Provisional Application Ser. No. 62/109,121, filed Jan. 29, 2015. These applications are hereby incorporated by reference herein.

This application claims benefit of priority to U.S. Appl. No. 62/109,121, filed on Jan. 29, 2015, which is incorporated by reference herein in its entirety.

This invention relates to ultrasonic diagnostic imaging systems and, in particular, to the use of blended fundamental and harmonic frequency ultrasonic images.

Harmonic imaging is used in ultrasonic imaging to image ultrasonic contrast agents and to overcome reverberation clutter which can occur at fundamental frequencies. While echo signals at higher harmonic frequencies will exhibit the attenuative effects of depth dependent frequency attenuation, today's ultrasound systems have sufficient sensitivity to largely overcome this drawback at shallower depths in the body. This effect is only prevalent in tissue harmonic imaging, where near field clutter as from rib artifacts is obviated by the slower development of harmonic signal components with depth. Harmonic contrast agents, on the other hand, elicit a strong harmonic response when stimulated by ultrasound, a response often even stronger than nearby fundamental frequency echo signals.

The depth dependent attenuation of the higher harmonic frequencies means that harmonic imaging will not produce a strong signal response with deeper penetration, limiting its effectiveness when imaging tissue and organs at significant depths in the body. An effective technique for dealing with this problem and realizing the benefits of both good resolution harmonic imaging and deep penetration fundamental imaging is described in U.S. Pat. No. 6,283,919 (Roundhill et al.) Roundhill et al. acquire both fundamental frequency and harmonic frequency signals from all depths and separate them by bandpass filtering. They then produce a blended image of the two types of signals. Preferably, the highly resolved, clutter-free harmonic signals predominate in the near field, while the deeper penetrating fundamental signals are used to the greatest degree in the far field. However, the filtering necessary to separate the fundamental and harmonic frequencies poses an undesirable tradeoff. To cleanly separate the signals into their two distinct bands, the bandwidth of the filters must be narrowly defined so that there is no band overlap, which particularly adversely limits the fundamental signals to a narrow band and resultant limited resolution. Widening the bands for more broadband imaging can cause the two bands to overlap and diminish the distinctive characteristics and benefits of each signal type. Accordingly it is desirable to be able to separate the fundamental and harmonic frequencies of the echo signals in a way which preserves the distinctiveness of each signal type while still affording broadband imaging with either type of signal.

In some aspects, the present invention includes ultrasound systems, such as an ultrasonic diagnostic imaging system for producing fundamental and harmonic frequency images. The systems can include an ultrasound imaging probe having an array transducer which transmits successive, differently modulated ultrasound pulses at a fundamental frequency and receives echo signals at fundamental and harmonic frequencies, a cancellation circuit, responsive to the received echo signals which additively and subtractively combines the echo signals from the differently modulated ultrasound pulses to produce separate fundamental and harmonic signals, a fundamental frequency filter having a passband which defines a band of fundamental frequency signals, a harmonic frequency filter having a passband overlapping the fundamental frequency passband which defines a band of harmonic frequency signals, a first detector which detects fundamental frequency image signals, a second detector which detects harmonic frequency image signals, a combiner which combines detected fundamental and harmonic frequency signals, and a display which displays blended fundamental and harmonic images.

In certain aspects, the ultrasound systems of the present invention can include an ultrasonic diagnostic imaging system for producing fundamental or harmonic frequency images that includes an ultrasound imaging probe having an array transducer which transmits successive, differently modulated ultrasound pulses at a fundamental frequency and receives echo signals at fundamental and harmonic frequencies, a cancellation circuit, responsive to the received echo signals which additively and subtractively combines the echo signals from the differently modulated ultrasound pulses to produce separate fundamental and harmonic signals, a fundamental frequency filter having a passband which defines a band of fundamental frequency signals, a harmonic frequency filter having a passband overlapping the fundamental frequency passband which defines a band of harmonic frequency signals, a detector, responsive to the band of fundamental frequency or harmonic frequency signals, which detects fundamental frequency or harmonic frequency image signals, a scan converter, responsive to detected fundamental or harmonic frequency image signals which produces a fundamental or harmonic image of a desired image format, and a display, coupled to the scan converter, which displays a fundamental or harmonic image.

In some aspects, the present invention includes an ultrasonic diagnostic imaging system for producing fundamental or harmonic frequency images, the system includes instructions thereon, which when executed cause the system to using an ultrasound imaging probe having an array transducer, transmit successive, differently modulated ultrasound pulses at a fundamental frequency and receive echo signals at fundamental and harmonic frequencies, additively and subtractively combine the echo signals from differently modulated ultrasound pulses to produce separate fundamental and harmonic signals, filter a band of fundamental frequency signals with a fundamental frequency filter having a passband, filter a band of harmonic frequency signals with a harmonic frequency filter having a passband overlapping the fundamental frequency passband, detect fundamental frequency or harmonic frequency image signals, produce a fundamental or harmonic image of a desired image format, and display a fundamental or harmonic image.

IN THE DRAWINGS

Figure 1:
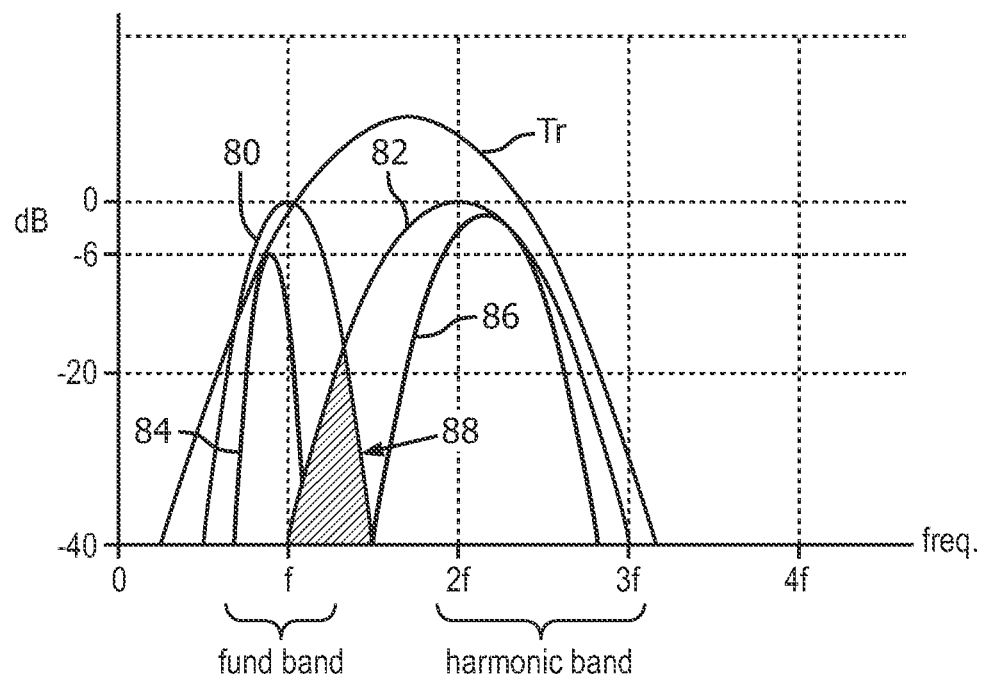
FIG. 1 is an illustration of filter separation of fundamental and harmonic frequency echo signal components.

In accordance with the principles of the present invention, an ultrasonic diagnostic imaging system is described which enable the clean separation of fundamental and harmonic signal components into distinct broadband signals. Two-pulse transmission can be used, transmitting the same pulse twice in succession to each point in an image region but in differently modulated forms. One example technique for doing this is called pulse inversion, in which the same pulse is transmitted with and without phase or polarity inversion. The transmit pulse has a broader bandwidth and a higher center frequency than conventionally used in pulse inversion. The received echo signals from the two transmissions are combined on a spatial basis by both addition and subtraction, resulting in two bands of frequencies, a harmonic band in which fundamental signal components have been cancelled and a fundamental band in which fundamental frequency components from the two echoes reinforce each other. The two bands are then bandpass filtered with filters that are allowed to overlap each other in frequency. Signals from the two bands are detected and combined into a blended fundamental/harmonic image, either before or after scan conversion. The result is an image with the combined benefits of both fundamental and harmonic imaging and with broadband image characteristics.

In some aspects, the present invention includes ultrasonic diagnostic imaging systems that produce fundamental and harmonic frequency images. In some embodiments, the systems can include an ultrasound imaging probe having an array transducer. The probe can be configured to transmit successive and differently modulated ultrasound pulses at a fundamental frequency. The differently modulated ultrasound pulses can, for example, be differently modulated in phase or polarity. The probe can also be configured to receive echo signals at fundamental and harmonic frequencies. In some aspects, the systems can include a beamformer, responsive to echo signals received by the array transducer, which produces coherent fundamental and harmonic frequency signals. The beamformer can include a multiline beamformer.

The systems can include a cancellation circuit, responsive to the received echo signals which additively and subtractively combines the echo signals from the differently modulated ultrasound pulses to produce separate fundamental and harmonic signals. In some embodiments, the cancellation circuit cancels fundamental frequency signals in a harmonic frequency band by pulse inversion. In some embodiments, the cancellation circuit can include a line buffer which stores echo signals received in response to the first of the successive ultrasound pulses, a first combining circuit which additively combines echo signals received in response to the second of the successive ultrasound pulses with echo signals stored by the line buffer, and a second combining circuit which subtractively combines echo signals received in response to the second of the successive ultrasound pulses with echo signals stored by the line buffer.

In certain aspects, the systems can include a fundamental frequency filter having a passband which defines a band of fundamental frequency signals, and a harmonic frequency filter having a passband overlapping the fundamental frequency passband which defines a band of harmonic frequency signals. The fundamental frequency filter can, for example, include a bandpass filter having a lower frequency passband and the harmonic frequency filter can include a bandpass filter having a higher frequency passband. In some embodiments, the array transducer exhibits a transducer passband, and the lower frequency passband is centered in the lower half of the transducer passband, and the higher frequency passband extends to the upper limit of the transducer passband.

In some aspects, the systems can include a first detector which detects fundamental frequency image signals, a second detector which detects harmonic frequency image signals, and a combiner which combines detected fundamental and harmonic frequency signals. Weighting circuits, coupled to receive detected fundamental and harmonic frequency signals, which relatively weights fundamental and harmonic frequency signals can also be used prior to combining by the combiner. The systems can include a display which displays blended fundamental and harmonic images.

In certain aspects, the systems can include a TGC circuit which amplifies signals in the band of fundamental frequency signals or signals in the band of harmonic frequency signals. The systems can also include a log amplifier which converts signals in the band of fundamental frequency signals or the band of harmonic frequency signals to logarithmically scaled signals.

In some embodiments, the systems of the present invention can include an ultrasound imaging probe having an array transducer which transmits successive, differently modulated ultrasound pulses at a fundamental frequency and receives echo signals at fundamental and harmonic frequencies, a cancellation circuit, responsive to the received echo signals which additively and subtractively combines the echo signals from the differently modulated ultrasound pulses to produce separate fundamental and harmonic signals, a fundamental frequency filter having a passband which defines a band of fundamental frequency signals, a harmonic frequency filter having a passband overlapping the fundamental frequency passband which defines a band of harmonic frequency signals, a detector, responsive to the band of fundamental frequency or harmonic frequency signals, which detects fundamental frequency or harmonic frequency image signals, a scan converter, responsive to detected fundamental or harmonic frequency image signals which produces a fundamental or harmonic image of a desired image format, and a display, coupled to the scan converter, which displays a fundamental or harmonic image.

FIG. 1 illustrates the passbands typical of an ultrasound system which separates fundamental and harmonic signals on the basis of frequency. This drawing illustrates a 46% transmit bandwidth frequency band centered at frequency "f" and shown as a thin black curve 80 in the drawing. The harmonic response to this waveform is plotted adjacent to the fundamental, also as a thin black curve 82. The transmit frequency and bandwidth are chosen so that both the fundamental and harmonic responses lie within the transducer's bandwidth, outlined by curve Tr.

The two wider outlined spectra 84 and 86 represent the receive bandpass shapes for the fundamental (on the left) and the harmonic (on the right) bands of frequencies. These two shapes are determined by the need to avoid frequencies where the fundamental and harmonic spectra overlap, and by the frequency limits imposed by the transducer passband Tr. It is seen that the fundamental spectrum 84 has a very narrow bandwidth, and the harmonic spectrum limits its lower frequency extent in order to avoid the frequency overlap region 88, cross-hatched in the drawing.

An important criterion for the success of fundamental-harmonic blending is that both components, when adequately received and detected, produce a good quality image. In the case of the spectra of FIG. 1, the fundamental image will be very low in frequency and very narrow in bandwidth as a result of the narrow band outlined by 84. This will not produce a very good image. The harmonic spectrum delineated by 86 looks much better, but is limited in penetration because it cannot include frequencies lower than those of the overlapped area 88. Thus, the overlapped area both limits the bandwidth of the fundamental frequencies and also the low frequencies of the harmonic spectrum, which would improve penetration.

Figure 2:
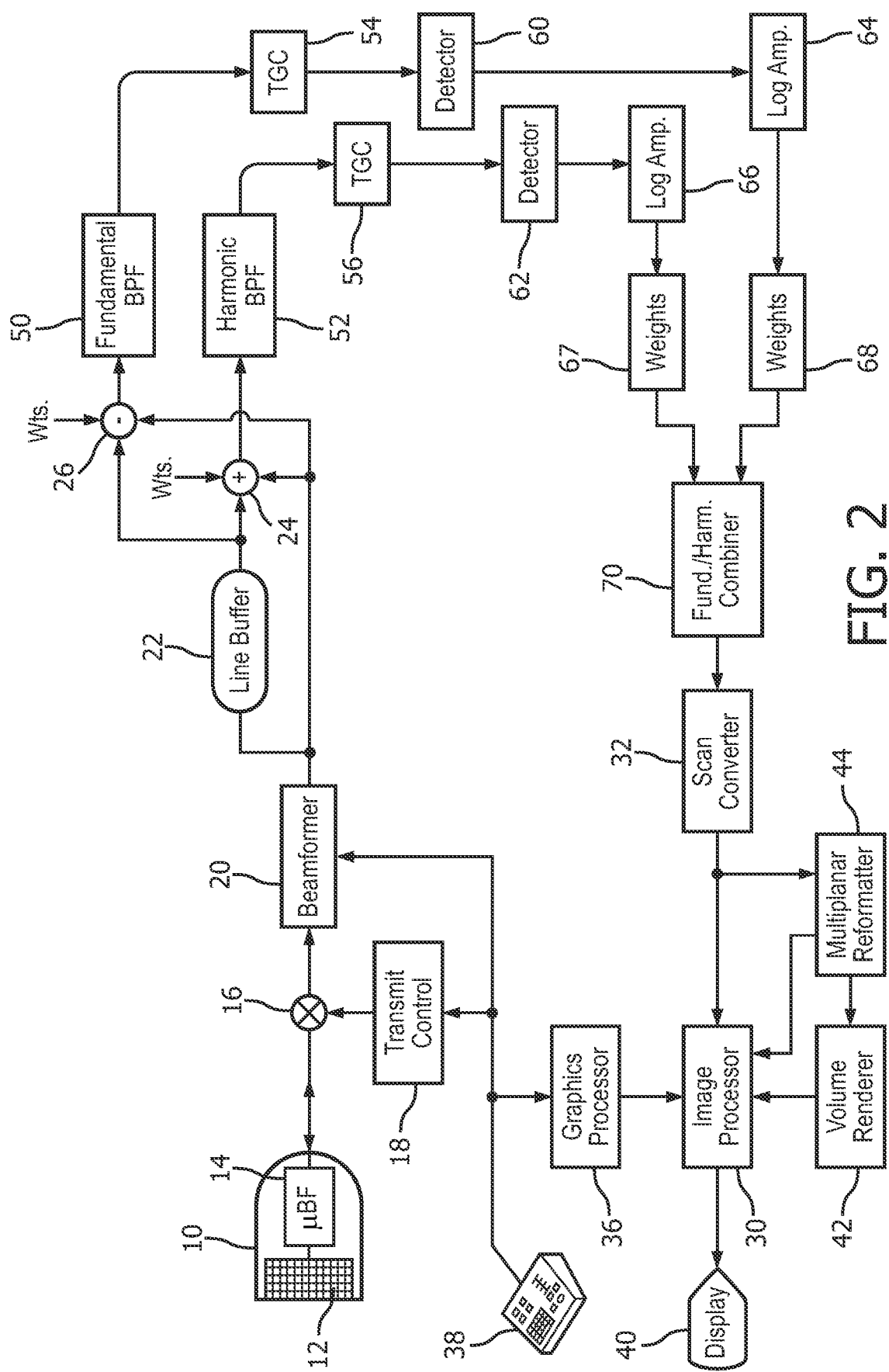
FIG. 2 illustrates in block diagram form an ultrasound system constructed in accordance with the principles of the present invention.

Referring now to FIG. 2, an ultrasonic diagnostic imaging system constructed in accordance with the principles of the present invention is shown in block diagram form. In FIG. 2 a transducer array 12 is provided in an ultrasound probe 10 for transmitting ultrasonic waves and receiving echo information. The transducer array 12 may be a one- or two-dimensional array of transducer elements capable of scanning in two or three dimensions, for instance, in both elevation (in 3D) and azimuth. The transducer array 12 is coupled to a microbeamformer 14 in the probe which controls transmission and reception of signals by the array elements. Microbeamformers are capable of at least partial beamforming of the signals received by groups or "patches" of transducer elements as described in U.S. Pat. No. 5,997, 479 (Savord et al.), U.S. Pat. No. 6,013,032 (Savord), and U.S. Pat. No. 6,623,432 (Powers et al.), which are hereby incorporated by reference in their entirety. The microbeamformer is coupled by the probe cable to a transmit/receive (T/R) switch 16 which switches between transmission and reception and protects the main beamformer 20 from high energy transmit signals. The transmission of ultrasonic beams from the transducer array 12 under control of the microbeamformer 14 is directed by a transmit controller 18 coupled to the T/R switch and the beamformer 20, which receives input from the user's operation of the user interface or control panel 38. Among the transmit characteristics controlled by the transmit controller are the amplitude, phase, and polarity of transmit waveforms. Beams formed in the direction of pulse transmission may be steered straight ahead from (orthogonal to) the transducer array, or at different angles for a wider field of view.

The echoes received by a contiguous group of transducer elements are beamformed by appropriately delaying them and then combining them. The partially beamformed signals produced by the microbeamformer 14 from each patch are coupled to a main beamformer 20 where partially beamformed signals from individual patches of transducer elements are combined into a fully beamformed signal. For example, the main beamformer 20 may have 128 channels, each of which receives a partially beamformed signal from a patch of 12 transducer elements. In this way the signals received by over 1500 transducer elements of a two dimensional array can contribute efficiently to a single beamformed signal.

In this implementation of the present invention the beamformed signals are coupled to a line buffer 22. The line buffer 22 stores the echo signals resulting from a pulse, such as those received following a positive polarity pulse of a positive-negative (uninverted/inverted) pulse pair transmitted in rapid succession for pulse inversion processing. When the second pulse of the differently modulated pulse pair is transmitted, the returning echoes are applied to a summer 24 and a subtractor 26 together with the spatially corresponding echoes of the previous pulse stored by the line buffer. This causes the echoes returned from a common point in the image field to be additively combined by the summer 24 and subtracted by the subtractor 26. The additive combination of echoes from oppositely phased or polarity transmit pulses by the summer 22 will result in the cancellation of fundamental frequency components and the production of harmonic frequency components. These harmonic signals are applied to a harmonic bandpass filter 52. The subtraction of echoes from oppositely phased or polarized pulses will result in the reinforcement of fundamental frequency components and elimination of harmonic content. These fundamental frequency signals are applied to a fundamental bandpass filter. Filtering signals in ultrasound applications is well known, and can be done using hardware, software, or both to process and filter ultrasound signals. Such techniques can be found, e.g., in Thomas Szabo, Diagnostic Ultrasound Imaging: Inside Out, Elsevier Academic Press, 2004, which is herein incorporated by reference in its entirety.

Figure 4:
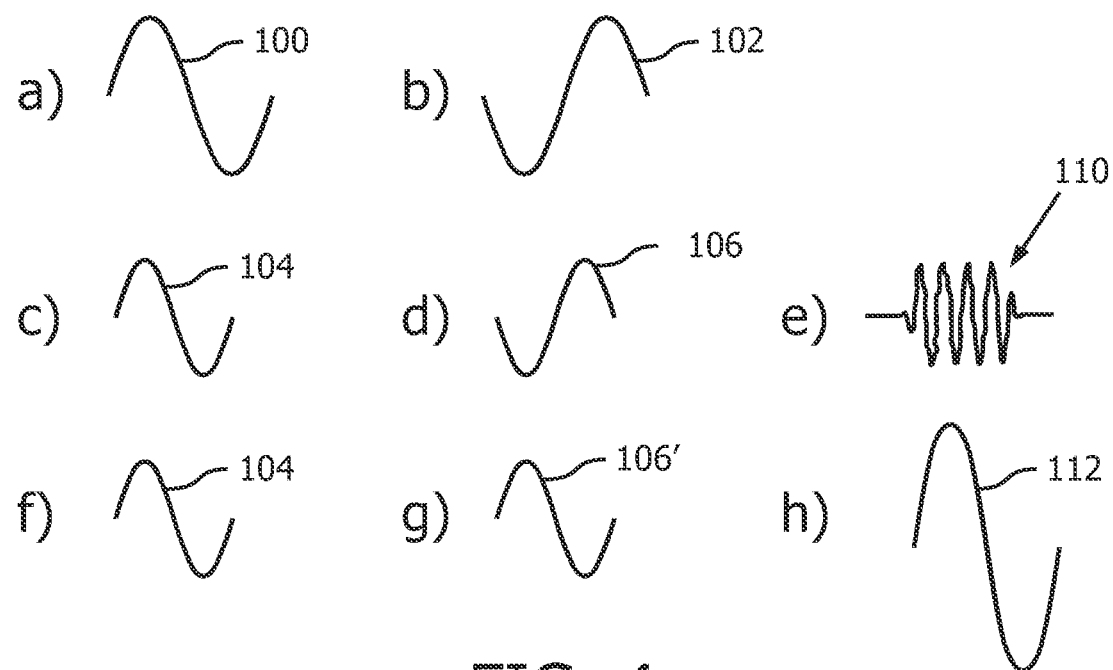
FIGS. 4a-4h illustrate a two-pulse imaging sequence suitable for use in an implementation of the present invention.
Figure 5:
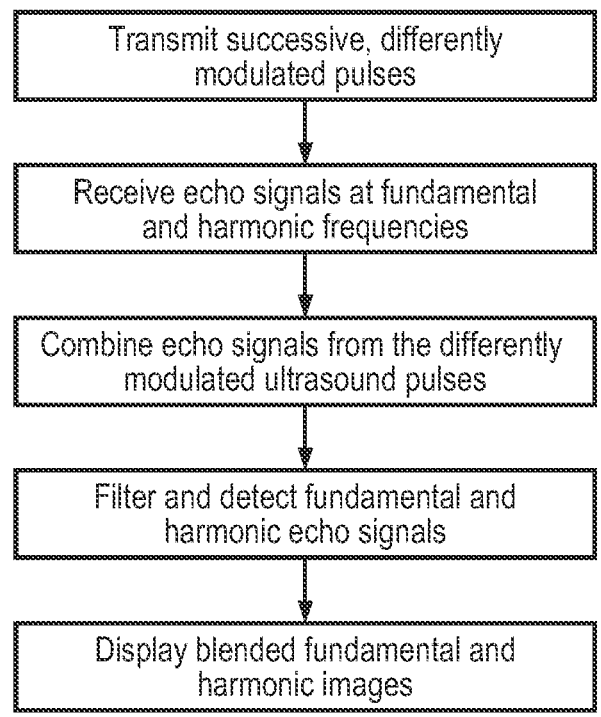
FIG. 5 illustrates a method in accordance with an implementation of the present invention.

FIG. 4 illustrates this signal cancellation phenomenon. This two-pulse sequence consists of a first pulse 100 and an oppositely phased or polarized pulse 102 transmitted sequentially in the same direction, that is they both insonify the same scanline in the image field. The differently modulated pulses are transmitted in rapid succession to minimize effects of inter-pulse motion; as soon as the echoes are received in response to the first pulse the second is transmitted. The two transmitted pulses are shown in FIGS. 4 *a*) and *b*).

The echoes received in response from a point in the image field are shown in FIGS. 4 *c*) and *d*). An echo 104 is produced in response to pulse 100, and an echo 106 is returned in response to pulse 102. When these two echoes are additively combined, this results in the cancellation of fundamental frequency components due to the opposing polarity. But left uncancelled and revealed by this combining are harmonic signal components 110 as shown at FIG. 4 *e*). These harmonic signals, left after cancellation of the fundamental frequency components, are applied to the harmonic bandpass filter 52.

Similarly, the echoes 104 returned from one of the pulses, shown in FIG. 4 *f*), are subtractively combined with the echoes from the other pulse. Echo 106' in FIG. 4 *g*) represents this subtractive combination by illustrating the second echo signal (i.e., 106) in inverted form. When echoes 104 and 106' are combined, this time the fundamental frequency components are the same and will additively combine and reinforce each other, as illustrated by fundamental frequency echo signal 112 in FIG. 4 *h*). These fundamental frequency signals are applied to the fundamental frequency bandpass filter 50. Thus, harmonic signals are produced by the cancellation of fundamental frequency components by one combiner (24), and fundamental frequency signals are produced by the other combiner (26).

Figure 3:
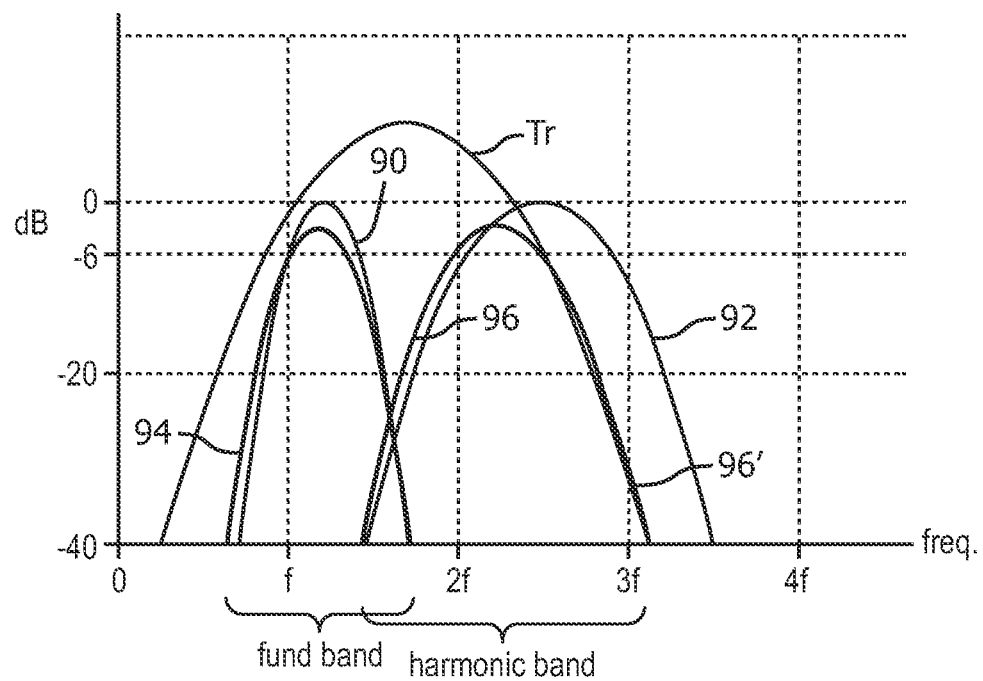
FIG. 3 is an illustration of signal component cancellation and bandpass filtering in accordance with the principles of the present invention.

Since the fundamental and harmonic signal components are separated by pulse inversion cancellation rather than by frequency selectivity, the respective bands can be shifted for improved performance as illustrated in FIG. 3. The fundamental frequency band 90 no longer is centered at frequency f as it was in FIG. 1, but is shifted higher in frequency as shown by the spectrum 90. The harmonic spectrum 92 is centered at twice the center frequency of the fundamental spectrum and it, too, occupies a broader band. In addition, the two spectra are allowed to overlap as FIG. 3 shows. This is acceptable because the components of the other spectrum are cancelled in each spectrum. As in FIG. 1, the transducer passband is illustrated by band Tr. The fundamental and harmonic bandpass filters 50 and 52 then filter the two overlapping spectra with the passband characteristics 94 and 96. It is seen that the filtered fundamental passband 94 is significantly wider than the limited passband 94 of FIG. 1, thereby producing broadband fundamental signals and images. The filtered harmonic passband 96 also exhibits a broad bandwidth. Since the harmonic spectrum 92 extends beyond the transducer passband Tr, the upper frequency skirt 96' of the harmonic band is effectively limited to the upper frequency skirt of the transducer passband Tr.

Following the fundamental and harmonic frequency bandpass filters 50 and 52, the two signal paths provide the same processing in each. Time gain control circuits 54 and 56 provide amplification with depth, the fundamental and harmonic signals are detected by detectors 60 and 62, and the signal amplitudes are logarithmically converted by log amplifiers 64 and 66. In accordance with a further aspect of the present invention, the fundamental and harmonic signals are combined by fundamental/harmonic combiner 70. The fundamental and harmonic signals at each point in the image field may be combined as they are produced by the log amps, but preferably they are weighted by weighting circuits 67 and 68. For instance, the harmonic signals may be more greatly weighted in the near field and the fundamental signals lesser so, and the reverse in the far field, in keeping with the idea of the Roundhill et al. patent to provide high resolution in the near field and greater penetration in the far field.

The blended fundamental/harmonic images produced by the combiner 70 are coupled to a scan converter 32 and a multiplanar reformatter 44. The scan converter arranges the echo signals in the spatial relationship from which they were received in a desired image format. For instance, the scan converter may arrange the echo signal into a two dimensional (2D) sector-shaped format, or a pyramidal three dimensional (3D) image when 3D scanning is performed. The scan converter can overlay a B mode structural image with colors corresponding to motion at points in the image field corresponding with their Doppler-estimated velocities to produce a color Doppler image which depicts the motion of tissue and blood flow in the image field. The multiplanar reformatter will convert echoes which are received from points in a common plane in a volumetric region of the body into an ultrasonic image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.) The 2D or 3D images are coupled from the scan converter 32, multiplanar reformatter 44, and volume renderer 42 to an image processor 30 for further enhancement, buffering and temporary storage for display on an image display 40. A graphic display overlay containing textual and other graphic information such as patient ID is produced by a graphics processor 36 for display with the ultrasound images.

In a preferred embodiment the beamformer 20 and the microbeamformer 14 perform multiline beamforming as described in U.S. Pat. No. 8,137,272 (Cooley et al.), which is herein incorporated by reference in its entirety. When implemented by multiline, a plurality of scanline positions are simultaneously insonified by each transmit pulse and the beamformer produces a plurality of scanlines of echoes in response to each pulse. The scanlines of each transmission are spatially aligned so that the corresponding echoes can be combined by pulse inversion to produce fundamental and harmonic signals along a plurality of scanlines in response to two pulse transmissions. The separated harmonic and fundamental signals are processed to produce images as described above.

Other variations will readily occur to those skilled in the art. For instance, the scan converter may precede the combiner 70, so that the fundamental and harmonic signals are first separately converted into the desired display format before blending. This enables separate display of the harmonic and fundamental images, if desired, before blending or without blending.

In some embodiments, the present invention further includes methods for producing fundamental and harmonic frequency images. The methods can include transmitting successive, differently modulated ultrasound pulses at a fundamental frequency and receiving echo signals at fundamental and harmonic frequencies. The methods include using a cancellation circuit, responsive to the received echo signals, to additively and subtractively combine the echo signals from the differently modulated ultrasound pulses to produce separate fundamental and harmonic signals. The methods include filtering (e.g., with a fundamental frequency filter) a band of fundamental frequency signals, and filtering (e.g., with a harmonic frequency filter) a band of harmonic frequency signals. The methods can include detecting the fundamental and harmonic frequency image signals, e.g., using one or more detectors. The methods can also include combining the detected fundamental and harmonic frequency image signals, and displaying blended fundamental and harmonic images.

It will be understood that each block of the block diagram illustrations, and combinations of blocks in the block diagram illustrations, as well any portion of the systems and methods disclosed herein, can be implemented by computer program instructions. These program instructions may be provided to a processor to produce a machine, such that the instructions, which execute on the processor, create means for implementing the actions specified in the block diagram block or blocks or described for the systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable hardware medium including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device. Processors can include hardware such as microprocessors, field programmable gate arrays (FPGAs), integrated circuits, or the like.

What is claimed is:

1. An ultrasonic diagnostic imaging system which produces fundamental and harmonic frequency images comprising:
    an ultrasound imaging probe having an array transducer and being configured to transmit successive, differently modulated ultrasound pulses at a fundamental frequency and to receive echo signals at fundamental and harmonic frequencies generated responsive to the ultrasound pulses, wherein a range of frequencies received by the array transducer is defined by a passband of the array transducer and wherein a portion of the echoes generated at the harmonic frequencies have a frequency greater than the passband;

a cancellation circuit that is responsive to the received echo signals and is configured to additively and subtractively combine the echo signals from the differently modulated ultrasound pulses to produce separate fundamental and harmonic signals;

a fundamental frequency filter having a passband defining a band of fundamental frequency signals configured to receive the separate fundamental signals from the cancellation circuit and provide fundamental frequency image signals based on the separate fundamental signals;

a harmonic frequency filter having a passband overlapping the fundamental frequency passband and defining a band of harmonic frequency signals configured to receive the separate harmonic signals from the cancellation circuit and provide harmonic frequency image signals based on the separate harmonic signals, wherein an upper frequency of the band of harmonic frequency signals is defined by the passband of the array transducer;

a first detector configured to detect the fundamental frequency image signals provided by the fundamental frequency filter;

a second detector configured to detect the harmonic frequency image signals provided by the harmonic frequency filter;

a combiner configured to combine the detected fundamental and harmonic frequency image signals; and a display for displaying blended fundamental and harmonic images generated from the combined detected fundamental and harmonic frequency image signals.

2. The ultrasonic diagnostic imaging system of claim 1, wherein the cancellation circuit is configured to cancel fundamental frequency signals in a harmonic frequency band by pulse inversion.

3. The ultrasonic diagnostic imaging system of claim 2, wherein the fundamental frequency filter comprises a bandpass filter having a lower frequency passband and wherein the harmonic frequency filter comprises a bandpass filter having a higher frequency passband.

4. The ultrasonic diagnostic imaging system of claim 3, wherein the array transducer comprises a transducer passband, wherein the lower frequency passband is centered in a lower half of the transducer passband; and wherein the higher frequency passband extends to an upper limit of the transducer passband.

5. The ultrasonic diagnostic imaging system of claim 3, wherein the differently modulated ultrasound pulses are differently modulated in phase or polarity.

6. The ultrasonic diagnostic imaging system of claim 5, wherein the cancellation circuit comprises a line buffer configured to store echo signals received in response to a first of the successive ultrasound pulses;

a first combining circuit configured to additively combine echo signals received in response to a second of the successive ultrasound pulses with echo signals stored by the line buffer; and a second combining circuit configured to subtractively combine echo signals received in response to the second of the successive ultrasound pulses with echo signals stored by the line buffer.

7. The ultrasonic diagnostic imaging system of 6, further comprising:

a TGC circuit configured to amplify signals in the band of fundamental frequency signals or signals in the band of harmonic frequency signals.

8. The ultrasonic diagnostic imaging system of claim 7, further comprising a log amplifier configured to convert signals in the band of fundamental frequency signals or the band of harmonic frequency signals to logarithmically scaled signals.

9. The ultrasonic diagnostic imaging system of claim 1, further comprising weighting circuits, coupled to receive the detected fundamental and harmonic frequency image signals, and configured to relatively weight the detected fundamental and harmonic frequency image signals prior to combining by the combiner.

10. The ultrasonic diagnostic imaging system of claim 1, further comprising a beamformer, responsive to the echo signals received by the array transducer, and configured to produce coherent fundamental and harmonic frequency signals.

11. The ultrasonic diagnostic imaging system of claim 10, wherein the beamformer comprises a multiline beamformer.

12. An ultrasonic diagnostic imaging system for producing fundamental or harmonic frequency images, the system comprising instructions thereon, which when executed cause the system to:

using an ultrasound imaging probe having an array transducer, transmit successive, differently modulated ultrasound pulses at a fundamental frequency and receive echo signals at fundamental and harmonic frequencies, generated responsive to the ultrasound pulses, wherein a range of frequencies received by the array transducer is defined by a passband of the array transducer and wherein a portion of the echoes generated at the harmonic frequencies have a frequency greater than the passband;

additively and subtractively combine the echo signals from the differently modulated ultrasound pulses to produce separate fundamental and harmonic signals;

filter a band of the separate fundamental frequency signals with a fundamental frequency filter having a passband to generate harmonic frequency image signals;

filter a band of the separate harmonic frequency signals with a harmonic frequency filter having a passband overlapping the fundamental frequency passband to generate harmonic frequency image signals, wherein an upper frequency of the band of harmonic frequency signals is defined by the passband of the array transducer;

detect the fundamental frequency image signals or the harmonic frequency image signals;

produce a fundamental image or a harmonic image of a desired image format from the fundamental image signals or the harmonic image signals; and display the fundamental or the harmonic image.

13. The ultrasonic diagnostic imaging system of claim 12, wherein the instructions further cause the system to cancel fundamental frequency signals in a harmonic frequency band by pulse inversion.

14. The ultrasonic diagnostic imaging system of claim 13, wherein the differently modulated ultrasound pulses are differently modulated in phase or polarity.

15. The ultrasonic diagnostic imaging system of claim 13, wherein the instructions further cause the system to produce coherent fundamental and harmonic frequency signals using a multiline beamformer.

* * * * *